(12) United States Patent
Fukuta

(10) Patent No.: US 8,543,186 B2
(45) Date of Patent: Sep. 24, 2013

(54) MAGNETIC RESONANCE IMAGING APPARATUS AND MAGNETIC RESONANCE IMAGING METHOD

(75) Inventor: Toshio Fukuta, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1107 days.

(21) Appl. No.: 12/039,787

(22) Filed: Feb. 29, 2008

(65) Prior Publication Data

US 2008/0214926 A1 Sep. 4, 2008

(30) Foreign Application Priority Data

Mar. 1, 2007 (JP) .................................. 2007-051753
Jan. 18, 2008 (JP) .................................. 2008-009022

(51) Int. Cl.
*A61B 5/05* (2006.01)

(52) U.S. Cl.
USPC ........................................................ 600/410

(58) Field of Classification Search
USPC ........................................................ 600/410
See application file for complete search history.

(56) References Cited

U.S. PATENT DOCUMENTS 5,514,957 A   5/1996 Tatebayashi
6,480,732 B1 * 11/2002 Tanaka et al. .................. 600/425

FOREIGN PATENT DOCUMENTS

| JP | 3-15457 | 3/1991 |
| JP | 7-311834 | 11/1995 |
| JP | 2002-272700 | 9/2002 |
| JP | 2006-34548 | 2/2006 |

OTHER PUBLICATIONS

Office Action (3 pgs.) dated Sep. 19, 2012 issued in corresponding Japanese Application No. 2008-009022 with an at least partial English-language translation thereof (3 pgs.).
Office Action (5 pgs.) dated Feb. 19, 2013 issued in corresponding Japanese Application No. 2008-009022 with an at least partial English-language translation thereof (9 pgs.).

* cited by examiner

*Primary Examiner* — Jacqueline Cheng
(74) *Attorney, Agent, or Firm* — Nixon & Vanderhye P.C.

(57) ABSTRACT

A magnetic resonance imaging apparatus includes a setting unit which sets a section position, a first image creating unit which creates a first image at the set section position by a multi planar reformat on the basis of a magnetic resonance signal collected from a subject by a first imaging sequence at a 3D region or multiple section positions different from the set section position, a determining unit which determines a section position of the first image, and a second image creating unit which creates a second image at the determined section position by the multi planar reformat on the basis of a magnetic resonance signal collected from the subject by a second imaging sequence different from the first imaging sequence at a 3D region or multiple section positions different from the determined section position.

9 Claims, 4 Drawing Sheets

MAGNETIC RESONANCE IMAGING APPARATUS AND MAGNETIC RESONANCE IMAGING METHOD

CROSS-REFERENCE TO RELATED APPLICATIONS

This application is based upon and claims the benefit of priority from prior Japanese Patent Applications No. 2007-051753, filed Mar. 1, 2007; and No. 2008-009022, filed Jan. 18, 2008, the entire contents of both of which are incorporated herein by reference.

BACKGROUND OF THE INVENTION

1. Field of the Invention

The present invention relates to a magnetic resonance imaging apparatus with a function of a multi planar reformat (hereinafter, referred to as 'MPR') and a magnetic resonance imaging method using the MPR.

2. Description of the Related Art

An MRI imaging technique can be largely classified into a 2-dimensional (2D) imaging technique and a 3-dimensional (3D) imaging technique. In such imaging techniques, an image of a planned section before a scanning operation is created and displayed. In the 2D imaging technique, a collection can be basically carried out in a multi-angle, and an offset, a slice thickness, a section direction for each sheet can be arbitrarily set. Meanwhile, in the 3D imaging technique, the same position information as that of the 2D imaging technique can be set for each slab, but a slice position for each slab is uniformly set by position information on the slab.

Additionally, there is a method in which an arbitrary section is cut out from 3D data collected by the 3D imaging technique by the MPR process. That is, an image of a cutout section assigned by a user through a GUI (graphical user interface) is created by the MPR process and displayed.

For example, JP-A-2002-272700 discloses a related technology.

In many cases, users want to see images obtained in different protocols in the same section state, in case of the same imaging portion. For example, many users want to fix a slice gap and a slice thickness in the 2D imaging technique even when an in-plane resolution changes. Meanwhile, in an axial imaging of a cervical vertebra and a lumbar vertebra, the 3D imaging technique using a SSFP (steady state free precession) has been frequently used in recent years. However, in the image obtained by the 3D imaging technique, it is difficult to see the same section as that of a T1 image obtained by the 2D imaging technique in a multi-angle or to develop that on a film. In many cases, users who interpret the image demand a film in which a shape of the same section is printed. Accordingly, in order to cope with such a demand in the current situation, a section image which is most similar to that of the 2D imaging technique is selected from the image obtained by the 3D imaging technique by an operator's eye sight, and then the selected image is printed on a film.

When the same sections as those of multiple sheets of images, which are obtained by the 2D technique in the state where the section direction, the offset, the slice thickness, etc. are arbitrarily changed to different values, are cutout by using the function of cutting out an arbitrary section from 3D data by the MPR process, a user necessarily selects each of multiple cutout sections, thereby increasing the user's burden.

Additionally, such inconvenience may occur in other cases. For example, there is a case where images, which are created by the MPR process on the basis of a plurality of 2D data or 3D data obtained by different sequences, are compared with each other. Additionally, there is another case where an image created by the MPR process in the past examination is compared with that created by the MPR process in the new examination.

BRIEF SUMMARY OF THE INVENTION

Under such a circumstance, it has been demanded that an image which is the same section as that of an image obtained by a 2D imaging technique or other MPR images is easily obtained by an MPR process.

According to a first aspect of the invention, there is provided a magnetic resonance imaging apparatus including: a setting unit which sets a section position; a first image creating unit which creates a first image at the set section position by a multi planar reformat on the basis of a magnetic resonance signal collected from a subject by a first imaging sequence at a 3D region or multiple section positions different from the set section position; a determining unit which determines a section position of the first image; and a second image creating unit which creates a second image at the determined section position by the multi planar reformat on the basis of a magnetic resonance signal collected from the subject by a second imaging sequence different from the first imaging sequence at a 3D region or multiple section positions different from the determined section position.

According to a second aspect of the invention, there is provided a magnetic resonance imaging apparatus including: a setting unit which sets a section position; a first image creating unit which creates a first image at the set section position on the basis of a magnetic resonance signal collected from a subject at the set section position; a determining unit which determines a section position of the first image; and a second image creating unit which creates a second image at the determined section position by a multi planar reformat on the basis of a magnetic resonance signal collected from the subject at a 3D region including at least a part of the determined section position.

According to a third aspect of the invention, there is provided a magnetic resonance imaging apparatus including: a determining unit which determines a section position of a first image created in the past by a multi planar reformat on the basis of a magnetic resonance signal collected from a subject at a 3D region or multiple section positions; and a second image creating unit which creates a second image at the determined section position by the multi planar reformat on the basis of a new magnetic resonance signal collected from the subject at the 3D region or multiple section positions.

According to a fourth aspect of the invention, there is provided a magnetic resonance imaging method including the steps of: setting a section position; creating a first image at the set section position by a multi planar reformat on the basis of a magnetic resonance signal collected from a subject by a first imaging sequence at a 3D region or multiple section positions different from the set section position; determining a section position of the first image; and creating a second image at the determined section position by the multi planar reformat on the basis of a magnetic resonance signal collected from the subject by a second imaging sequence different from the first imaging sequence at a 3D region or multiple section positions different from the determined section position.

According to a fifth aspect of the invention, there is provided a magnetic resonance imaging method including the steps of: setting a section position; creating a first image at the set section position on the basis of a magnetic resonance signal collected from a subject at the set section position;

determining a section position of the first image; and creating a second image at the determined section position by a multi planar reformat on the basis of a magnetic resonance signal collected from the subject at a 3D region including at least a part of the determined section position.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Hereinafter, an exemplary embodiment of the invention will be described with reference to the accompanying drawings.

Figure 1:
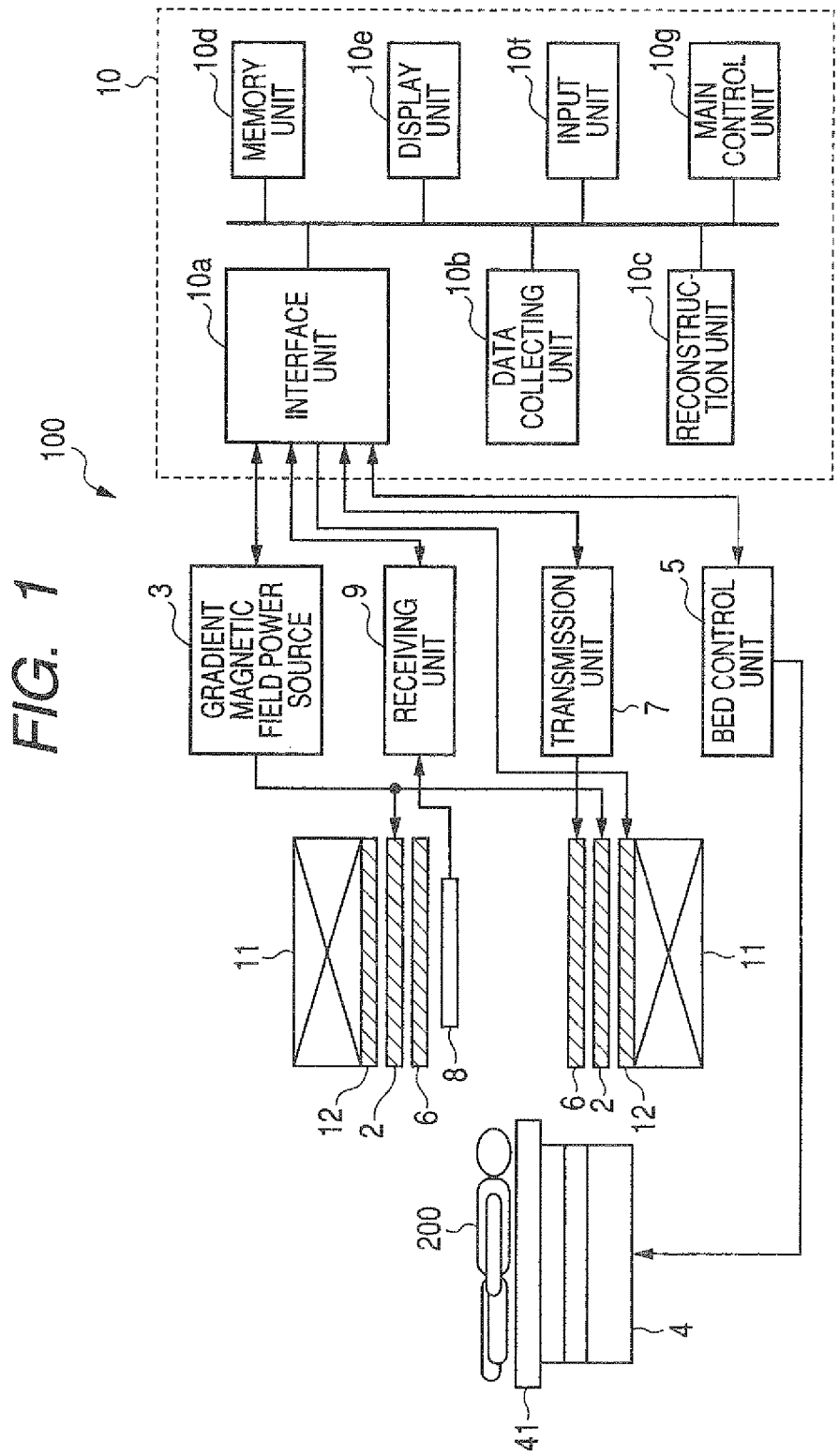
FIG. 1 is a view illustrating a configuration of a magnetic resonance imaging apparatus (MRI apparatus) 100 according to an exemplary embodiment of the invention.

FIG. 1 is a view illustrating a configuration of a magnetic resonance imaging apparatus (MRI apparatus) 100 according to an exemplary embodiment of the invention. The MRI apparatus 100 includes a static magnetic field magnet unit 1, a gradient magnetic field coil 2, a gradient magnetic field power source 3, a bed 4, a bed control unit 5, a transmission RF coil 6, a transmission unit 7, a receiving RF coil 8, a receiving unit 9, and a computer system 10.

The static magnetic field magnet unit 1 is formed in a hollow cylindrical shape, and generates a uniform static magnetic field in a space therein. The static magnetic field magnet unit 1 includes a static magnetic field magnet 11 and a correction coil 12. As the static magnetic field magnet 11, for example, a permanent magnet or a super conducting magnet is used. The correction coil 12 is configured in the manner that multiple coils are combined. The correction coil 12 generates a correction magnetic field for correcting a uniformity of the static magnetic field that is generated by the static magnetic field magnet 11.

The gradient magnetic field coil 2 is formed in a hollow cylindrical shape and is disposed inside the static magnetic field magnet unit 1. In the gradient magnetic field coil 2, three types of coils corresponding to X, Y, and Z axes which intersect each other are combined. The gradient magnetic field coil 2 generates a gradient magnetic field of which a magnetic-field magnitude changes along the X, Y, and Z axes when the gradient magnetic field power source 3 individually supplies current to each of the three types of coils. Additionally, the direction in the Z axis, for example, is set to the same direction as that of the static magnetic field. The gradient magnetic fields in the X, Y, and Z axes are arbitrarily used, for example, as a slice selection gradient magnetic field Gs, a phase encoding gradient magnetic field Ge, and a lead-out gradient magnetic field Gr, respectively. The slice selection gradient magnetic field Gs is used to arbitrarily decide an imaging section. The phase encoding gradient magnetic field Ge is used to change a phase of a magnetic resonance signal in accordance with a spatial location. The lead-out gradient magnetic field Gr is used to change a frequency of the magnetic resonance signal in accordance with the spatial location.

A subject 200 is allowed to enter the hollow (imaging space) of the gradient magnetic field coil 2 while being placed on a top plate 41 of the bed 4. The top plate 41 is driven by the bed control unit 5 so that the bed 4 moves in the longitudinal direction and the vertical direction. In general, the bed 4 is installed so that a central axis of the static magnetic field magnet 1 is in parallel to the longitudinal direction.

The transmission RF coil 6 is disposed inside the gradient magnetic field coil 2. The transmission RF coil 6 generates a high-frequency magnetic field upon receiving a high-frequency pulse from the transmission unit 7.

The transmission unit 7 transmits a high-frequency pulse corresponding to a Larmor frequency to the transmission RF coil 6.

The receiving RF coil 8 is disposed inside the gradient magnetic field coil 2. The receiving RF coil 8 receives a magnetic resonance signal that is radiated from the subject influenced by the high-frequency magnetic field. An output signal from the receiving RF coil 8 is input to the receiving unit 9.

The receiving unit 9 creates magnetic resonance signal data on the basis of the output signal from the receiving RF coil 8.

The computer system 10 includes an interface unit 10a, a data collecting unit 10b, a reconstruction unit 10c, a memory unit 10d, a display unit 10e, an input unit 10f, and a main control unit 10g.

The interface unit 10a is connected to the gradient magnetic field power source 3, the bed control unit 5, the transmission unit 7, the receiving RF coil 8, the receiving unit 9, etc. The interface unit 10a inputs and outputs signals that are transmitted and received between the respective connected units and the computer system 10.

The data collecting unit 10b collects digital signals output from the receiving unit 9 through the interface unit 10a. The data collecting unit 10b stores the collected digital signals, that is, magnetic resonance signal data in the memory unit 10d. The data collecting unit 10b collects magnetic resonance data inside region of interest (ROI) under the control of the main control unit 10g upon collecting data for calculating a correction amount of the static magnetic field. In this way, the data collecting unit 10b configures a collector together with the main control unit 10g.

The reconstruction unit 10c performs a reconstruction such as a post process, that is, a Fourier transform on the magnetic resonance signal data stored in the memory unit 10d, so that spectrum data or image data of a desired nuclear spin in the subject 200 is obtained.

The memory unit 10d stores the magnetic resonance signal data, and the spectrum data or the image data for each patient. Additionally, the memory unit 10d stores cutout section information on a cutout section of a section image that is generated by the past MPR.

Under a control of the main control unit 10g, the display unit 10e displays various information such as the spectrum data or the image data. As the display unit 10e, a display device such as a liquid crystal display device may be used.

The input unit 10f inputs various instructions or information in accordance with an operator's operation. As the input unit 10f, a pointing device such as a mouse or a track ball, a selection device such as a mode switch, or an input device such as a keyboard may be appropriately used.

The main control unit 10g includes a CPU, a memory, and the like that are not shown in the drawing, and generally controls the respective units of the MRI apparatus 100. Additionally, the main control unit 10g has the following characteristic functions according to the embodiment, in addition to the functions for controlling the respective units to realize general operations that are provided in a known MRI apparatus by using the MRI apparatus 100. Specifically, the main control unit 10g sets an imaging section in a 2D imaging technique in accordance with the operator's instruction that is input from the input unit 10f. The main control unit 10g controls the gradient magnetic field power source 3, the bed control unit 5, the transmission unit 7, the receiving unit 9, and the data collecting unit 10b to collect the magnetic resonance data for the imaging section. The main control unit 10g controls the reconstruction unit 10c to reconstruct a 2D image of the imaging section on the basis of the magnetic resonance data collected from the imaging section. The main control unit 10g sets a 3D region in accordance with the operator's instruction that is input from the input unit 10f. The main control unit 10g controls the gradient magnetic field power source 3, the bed control unit 5, the transmission unit 7, the receiving unit 9, and the data collecting unit 10b to collect a magnetic resonance signal from the 3D region. The main control unit 10g sets a region where the 3D region overlaps with the imaging section to the cutout section. The main control unit 10g sets a region where the 3D region overlaps with the cutout section indicated by the cutout section information that is stored in the memory unit 10d to a new cutout section. The main control unit 10g sets a region where the 3D region overlaps with the imaging section or a region where the 3D region overlaps with the cutout section indicated by the cutout section information stored in the memory unit 10d to a cutout section candidate. The main control unit 10g displays an image showing the cutout section candidate on the display unit 10e. The main control unit 10g sets the cutout section in accordance with the operator's instruction that is input from the input unit 10f. The main control unit 10g controls the reconstruction unit 10c to create a section image of the cutout section by use of the MPR based on the magnetic resonance data collected from the 3D region.

Next, an operation of the MRI apparatus 100 with such a configuration will be described.

Figure 2:
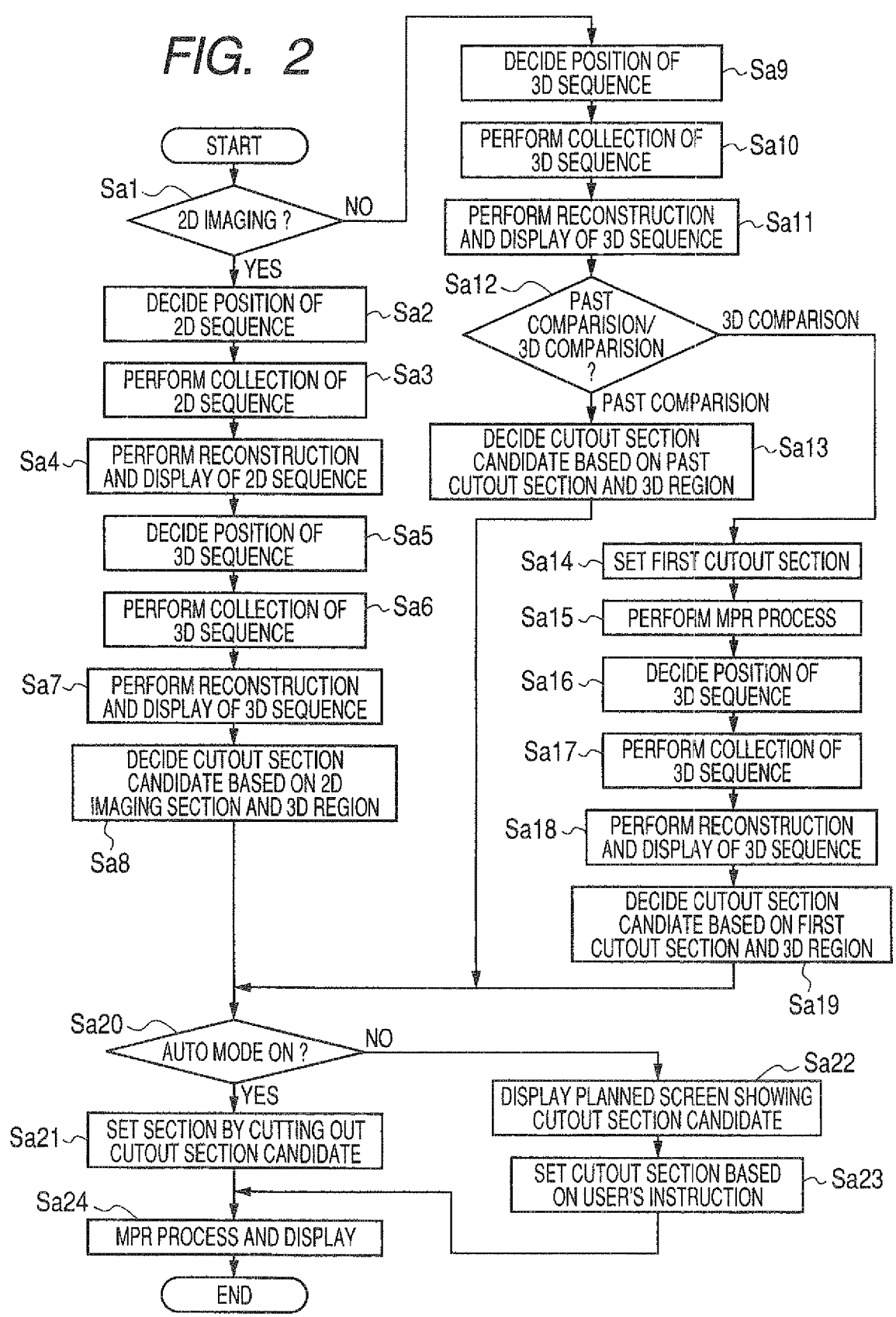
FIG. 2 is a flowchart illustrating a main control unit 10g performing a 3D imaging technique and displaying an image obtained by the 3D imaging technique in the form of a section image obtained by an MPR process.

The main control unit 10g performs the processes shown in FIG. 2 in accordance with the operator's instruction so that the 3D imaging technique is carried out and the 3D imaging result is displayed in the form of the section image obtained by the MPR process.

In STEP Sa1, the main control unit 10g checks whether the 2D imaging technique is set to be carried out. Additionally, the setting operation is carried out by the operator, in accordance with the above-described instruction.

Figure 3:
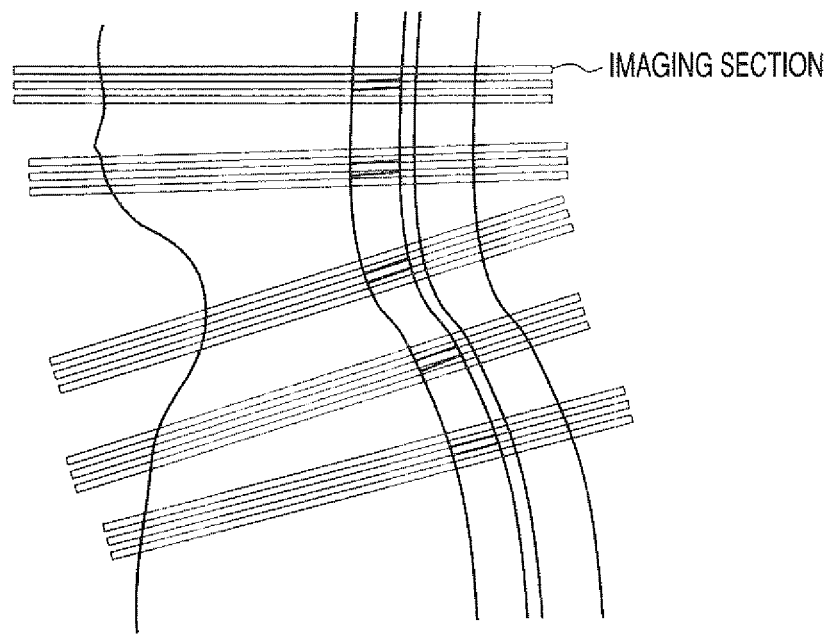
FIG. 3 is a view illustrating an imaging section setting state in a 2D sequence.

When the 2D imaging technique is set, the main control unit 10g advances from STEP Sa1 to STEP Sa2. In STEP Sa2, the main control unit 10g decides a position of the 2D sequence in accordance with the operator's instruction input from the input unit 10f, and sets a position of the imaging section (a slice central position, a slice direction, a slice thickness, etc.). FIG. 3 is a view illustrating an imaging section setting state in the 2D sequence. Additionally, FIG. 3 illustrates an imaging section for a 2D multi-angle imaging technique.

In STEP Sa3, the main control unit 10g controls the respective units to collect the magnetic resonance data by the 2D sequence from the imaging section set in STEP Sa2. In STEP Sa4, the main control unit 10g controls the reconstruction unit 10c to perform a reconstruction process of the 2D sequence, and thus displays the reconstructed 2D image on the display unit 10e. At this timer the reconstruction unit 10c performs the reconstruction process on the basis of the magnetic resonance data collected by the data collecting unit 10b in STEP Sa2.

Figure 4:
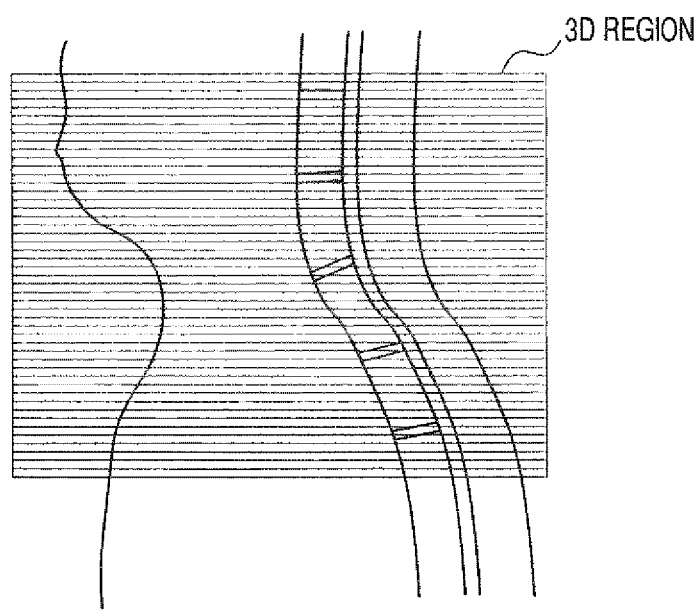
FIG. 4 is a view illustrating a state where a 3D region as an imaging target in a 3D sequence and a collection section are set.

In STEP Sa5, the main control unit 10g decides a position of the 3D sequence and sets a 3D region as a 3D imaging target and a section in which the magnetic resonance data is collected from the 3D region. FIG. 4 is a view illustrating a state where the 3D region as the imaging target in the 3D sequence and the collection section are set. In STEP Sa 6, the main control unit 10g controls the respective units to collect the magnetic resonance data by the 3D sequence. In STEP Sa7, the main control unit 10g controls the reconstruction unit 10c to perform a reconstruction process of the 3D sequence, and thus displays the reconstructed 3D image on the display unit 10e. At this time, the reconstruction unit 10c performs the reconstruction process on the basis of the magnetic resonance data collected by the data collecting unit 10b in STEP Sa6.

Figure 5:
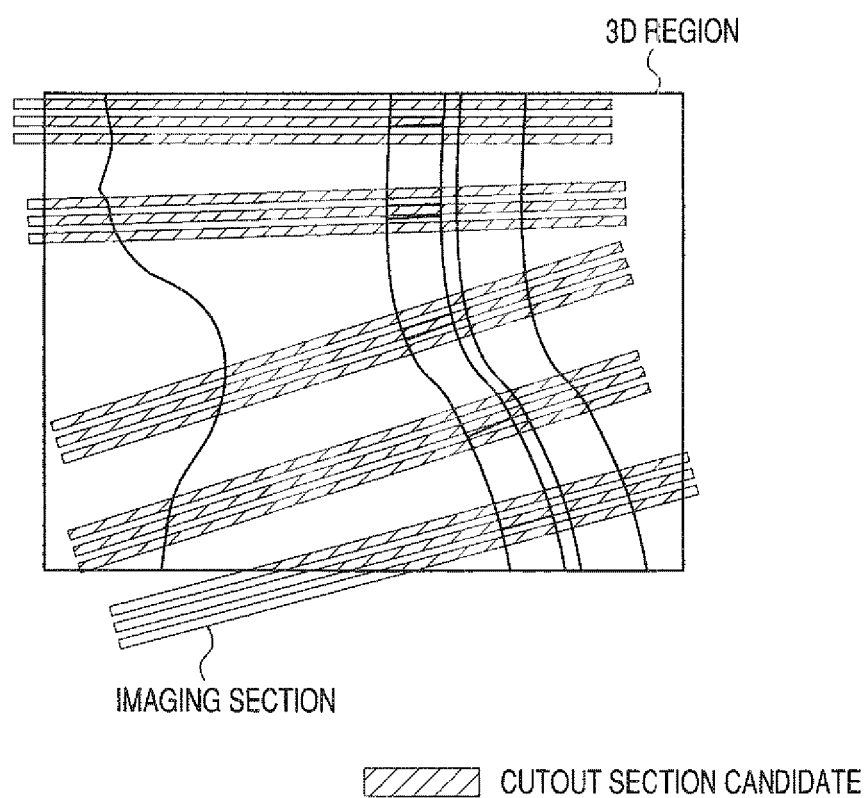
FIG. 5 is a view illustrating a cutout section candidate.

In STEP Sa8, the main control unit 10g sets the cutout section candidate on the basis of the 2D imaging section set in STEP Sa2 and the 3D region set in STEP Sa5. Specifically, the main control unit 10g sets a region where the 3D region overlaps with the 2D imaging section to the cutout section candidate. Accordingly, when the 2D imaging section set in STEP Sa2 and the 3D region set in STEP Sa5 are in the states shown in FIGS. 3 and 4, respectively, the cutout section candidate can be set to a hatching region shown in FIG. 5.

On the other hand, when the 2D imaging technique is not set, the main control unit 10g advances from STEP Sa1 to STEP Sa9. Subsequently, in STEP Sa9 to STEP Sa11, the main control unit 10g performs the 3D imaging technique in the same manner shown in STEP Sa5 to STEP Sa7. Subsequently, in STEP Sa12, the main control unit 10g checks whether a past comparison is set to be carried out or a 3D comparison is set to be carried out. The setting operation is carried out by the operator, in accordance with the above-described instruction. Additionally, the past comparison is to compare the MPR image based on the current 3D imaging technique with the MPR image for the past examination. Further, the 3D comparison is to compare the MPR image based on the 3D imaging technique in STEP Sa9 to STEP Sa11 with the MPR image based on a 3D imaging technique described below.

When the past comparison is set, the main control unit 10g advances from STEP Sa12 to STEP Sa13. In STEP Sa13, the main control unit 10g sets a region where the 3D region overlaps with the past cutout section to the cutout section candidate. At this time, the past cutout section corresponds to the cutout section that is indicated by the cutout section information stored in the memory unit 10d. That is, the past cutout section corresponds to the cutout section to which the past MPR process is carried out. When the cutout section information on a plurality of MPR processes is stored in the memory unit 10d, for example, the cutout section indicated by the cutout section information that is selected by the operator is set to the past cutout section.

When the 3D comparison is set, the main control unit 10g advances from STEP Sa12 to STEP Sa14. In STEP Sa14, the main control unit 10*g* sets a first cutout section on the basis of the operator's instruction. The first cutout section is set for the MPR processes based on the 3D imaging technique in STEP Sa9 to STEP Sa11. Additionally, in STEP Sa15, the main control unit 10*g* creates the MPR image of the cutout section set in Sa14 by the MPR process.

Subsequently, the main control unit 10*g* performs the 3D imaging technique in STEP Sa16 to STEP Sa18 in the same manner shown in STEP Sa5 to Sa7. In general, the 3D imaging technique is carried out by a sequence different from that of the 3D imaging technique in STEP Sa9 to STEP Sa11. At this time, the sequence used for the 3D imaging technique is arbitrarily set by, for example, the operator. Subsequently, in STEP Sa19, the main control unit 10*g* sets a region where the 3D region overlaps with the first cutout section to the cutout section candidate.

In STEP Sa8, STEP Sa13, or STEP Sa19, when the cutout section candidate has been set, the main control unit 10*g* advances to STEP Sa20. In STEP Sa20, the main control unit 10*g* checks whether an auto mode for setting the cutout section candidate is in an ON state. Subsequently, when the auto mode is in an ON state, the main control unit 10*g* advances from STEP Sa20 to STEP Sa21. In STEP Sa21, the main control unit 10*g* sets the cutout section candidate in STEP Sa8 to Sa13 to the cutout section. On the other hand, when the auto mode is in an OFF state, the main control unit 10*g* advances from STEP Sa20 to STEP Sa22. In STEP Sa22, the main control unit 10*g* displays a planned screen showing the cutout section candidate on the display unit 10*e*. The operator assigns a desired cutout section by referring to the cutout section candidate displayed on the display unit 10*e*. Subsequently, in STEP Sa23, the main control unit 10*g* assigns the cutout section in accordance with the operator's instruction. Additionally, the operator may assign a totally new cutout section by referring to the displayed cutout section candidate, or may modify the cutout section candidate if necessary.

In STEP Sa21 or STEP Sa23, when the cutout section has been set, the main control unit 10*g* advances to STEP Sa24. In STEP Sa24, the main control unit 10*g* creates the MPR image of the cutout section set in STEP Sa21 or STEP Sa23 by the MPR process, and thus displays the MPR image on the display unit 10*e*. Additionally, it is possible to develop the MPR image on a film by using a filming device (not shown) attached to the outside of the MRI apparatus 100.

According to the above-described embodiment, when the 2D imaging technique is carried out and then the auto mode is set in an ON state, a region where the 3D region as the 3D imaging target overlaps with the imaging section that is set for the 2D imaging technique is automatically set to the cutout section. Accordingly, it is possible to set the cutout section for obtaining the MPR image that is the same section as that of the 2D image obtained by the 2D imaging technique without any determination or operation performed by the operator.

According to the above-described embodiment, when the 2D imaging technique is not carried out, the past comparison is carried out, and then the auto mode is set in an ON state. A region where the 3D region as the 3D imaging target overlaps with the cutout section that has been subjected to the past MPR process is automatically set to a new cutout section. Accordingly, it is possible to set the cutout section for obtaining the MPR image that is the same section as that of the MPR image created in the past without any determination or operation performed by the operator.

According to the above-described embodiment, when the 2D imaging technique is not carried out, the 3D comparison is carried out, and then the auto mode is set in an ON state. A region among the 3D regions as the latter 3D imaging target and which overlaps with the cutout section that is set for the former 3D imaging technique is automatically set to the cutout section for the MPR process in the latter 3D imaging technique. Accordingly, it is possible to set the cutout section for obtaining the MPR image that is the same section as that of the MPR image created in the former 3D imaging using a different sequence without any determination or operation performed by the operator.

According to the above-described embodiment, when the 2D imaging technique is carried out and then the auto mode is set in an OFF state, a region where the 3D region as the 3D imaging target overlaps with the imaging section that is set for the 2D imaging technique is set to the cutout section candidate, and thus is provided for the operator. Accordingly, it is possible for the operator to plan the MPR process by referring to the cutout section for obtaining the MPR image that is the same section as that of the 2D image obtained by the 2D imaging technique.

According to the above-described embodiment, when the 2D imaging technique is not carried out, the past comparison is carried out, and then the auto mode is set in an OFF state. A region where the 3D region as the 3D imaging target overlaps with the cutout section that has been subjected to the past MPR process is set to a new cutout section candidate, and thus is provided for the operator. Accordingly, it is possible for the operator to plan the MPR process by referring to the cutout section for obtaining the MPR image that is the same section as that of the MPR image created in the past.

According to the above-described embodiment, when the 2D imaging technique is not carried out, the 3D comparison is carried out, and then the auto mode is set in an OFF state. A region where the 3D region as the latter 3D imaging target overlaps with the cutout section that is set for the former 3D imaging technique is set to the cutout section candidate for the MPR process in the latter 3D imaging technique. Accordingly, it is possible for the operator to plan the MPR process in the latter 3D imaging technique by referring to the cutout section for obtaining the MPR image that is the same section as that of the MPR image created in the former 3D imaging technique.

According to the above-described embodiment, since the MPR image is created for the cutout section that is automatically set in the aforementioned-manner or the cutout section that is set on the basis of a plan performed by the operator in the aforementioned-manner, it is possible to easily obtain the image that is the same section as that of the image obtained by the 2D imaging technique or other MPR images by use of the MPR process.

The above-described embodiment may be modified into various forms as below.

In the operation for automatically setting the cutout section based on the 2D imaging section, the operation for automatically setting the cutout section based on the past cutout section, the operation for suggesting the cutout section candidate based on the 2D imaging section, and the operation for suggesting the cutout section candidate based on the past cutout section, one or three of them may be carried out.

In STEP Sa8 or STEP Sa13, the 2D imaging section or the past cutout section may be directly set to the cutout section candidate.

Since a region where the 3D region overlaps with the 2D imaging section is set to the cutout section, the 2D imaging section outside the 3D region is not identical with the cutout section set based on the 2D section. Accordingly, it is possible to inform the operator that the cutout section is not identical with the 2D section at the time of displaying the MPR image created from such a cutout section. The informing operation may be arbitrarily carried out by a non-identical region displayed in the MPR image, a mark, a text message, an alarming sounds or a voice message.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A magnetic resonance imaging apparatus comprising:
   a setting unit configured to set a first section position;
   an image creating unit configured to create a first image at the first section position based on magnetic resonance signals collected from a subject by a first imaging sequence or on the basis of images based on the magnetic resonance signals and to create a second 3D image based on magnetic resonance signals collected from the subject by a second imaging sequence different from the first imaging sequence for a 3D region that at least partially overlaps with the first section position;
   a determining unit configured to determine a second section position corresponding to where the first image and second image overlap one another; and
   said image creating unit further configured to create a third image at the second section position using a multi planar reformat process on the second 3D image.

2. The magnetic resonance imaging apparatus according to claim 1, further comprising:
   a providing unit configured to provide the second section position determined by the determining unit to an operator; wherein
   said setting unit is configured to set a third section position for the multi planar reformat process in accordance with an operator's instruction, and
   the image creating unit is configured to create the third image at the third section position using the multi planar reformat process.

3. The magnetic resonance imaging apparatus according to claim 2, wherein the image creating unit is configured to create the third image based on the magnetic resonance signals collected for the 3D region and only at a region where the 3D region overlaps with the third section position.

4. A magnetic resonance imaging apparatus as in claim 1, wherein:
   the first image created by the image creating unit is a image created in the past by a multi planar reformat process performed on the basis of magnetic resonance signals collected from a subject for a 3D region or multiple section positions.

5. The magnetic resonance imaging apparatus according to claim 4, further comprising:
   a memory unit configured to store information on a section position of the first image, which is created in the past, wherein the determining unit is configured to determine the first section position of the first image, created in the past, on the basis of the information stored in the memory unit.

6. The magnetic resonance imaging apparatus according to claim 4, further comprising:
   a providing unit configured to provide the second section position determined by the determining unit to an operator; wherein
   said setting unit is configured to set a third section position for the multi planar reformat process in accordance with an operator's instruction, and
   the image creating unit is configured to create the third image at the third section position set using the multi planar reformat process.

7. The magnetic resonance imaging apparatus according to claim 6, wherein the image creating unit is configured to create the third image only at a region where the 3D region overlaps with the third section position set by the setting unit.

8. The magnetic resonance imaging apparatus according to claim 1 wherein the first image created by the image creating unit is a 3D image.

9. A magnetic resonance imaging method comprising:
   setting a first section position;
   creating a first image at the set first section position based on magnetic resonance signals collected from a subject by a first imaging sequence or on the basis of images based on the magnetic resonance signals, and creating a second 3D image based on magnetic resonance signals collected from the subject by a second imaging sequence different from the first imaging sequence for a 3D region that at least partially overlaps with the first section position;
   determining a second section position corresponding to where the first image and the second image overlap one another; and
   creating a third image at the determined second section position using a multi planar reformat process on the second 3D image.

* * * * *